(12) United States Patent
Wilkins

(10) Patent No.: US 6,523,009 B1
(45) Date of Patent: Feb. 18, 2003

(54) INDIVIDUALIZED PATIENT ELECTRONIC MEDICAL RECORDS SYSTEM

(76) Inventor: Bobbi L. Wilkins, 408 Lynchester Ct., Raleigh, NC (US) 27615

( * ) Notice: Subject to any disclaimer, the term of this patent is extended or adjusted under 35 U.S.C. 154(b) by 0 days.

(21) Appl. No.: 09/435,499

(22) Filed: Nov. 6, 1999

(51) Int. Cl.⁷ .............................................. G06F 17/60
(52) U.S. Cl. ................................................ 705/3; 705/2
(58) Field of Search ............................. 705/1, 2, 3, 4; 600/300, 301

(56) References Cited

U.S. PATENT DOCUMENTS

| | | | |
|---|---|---|---|
| 5,235,702 A | | 8/1993 | Miller |
| 5,327,341 A | * | 7/1994 | Whalen et al. ................. 705/2 |
| 5,572,421 A | * | 11/1996 | Altman et al. ................. 705/3 |
| 5,664,109 A | | 9/1997 | Johnson et al. |
| 5,715,451 A | | 2/1998 | Marlin |
| 5,724,580 A | | 3/1998 | Levin et al. |
| 5,826,237 A | | 10/1998 | Macrae et al. |
| 5,845,255 A | * | 12/1998 | Mayaud .......................... 705/3 |
| 5,867,821 A | * | 2/1999 | Ballantyne et al. ............. 705/2 |
| 5,890,129 A | | 3/1999 | Spurgeon |
| 5,924,074 A | | 7/1999 | Evans |
| 6,154,726 A | * | 11/2000 | Rensimer et al. ............... 705/2 |

* cited by examiner

Primary Examiner—Sam Rimell
(74) Attorney, Agent, or Firm—Glasgow Law Firm, PLLC

(57) ABSTRACT

An individualized patient electronic medical records system that provides unlimited patient access to her/his medical records, including text and other data. Additionally, the invention may include a benchmark against which medical treatments can be evaluated for compliance with reasonable standard of care or a prompt to indicate appropriate testing, medications, etc., based upon the patient's age, sex, etc. Also, the invention is applicable to human patients and to animal patients. Advantages of the invention include patient ownership, control, and access to her/his individual records at any time. Also, the patient can review and enter comments or questions on her/his data record for review and consideration by a physician. Furthermore, the patient can carry the medical record on her/his person so that the information is readily accessible in the event of an emergency or if s/he were traveling. Finally, any entry to the medical records is coded or identified by the provider or patient her/himself, and a password or other write-protect means prevents tampering or altering information entered by someone else.

56 Claims, 2 Drawing Sheets

INDIVIDUALIZED PATIENT ELECTRONIC MEDICAL RECORDS SYSTEM

BACKGROUND OF THE INVENTION (1) Field of the Invention

The present invention relates generally to electronic medical records, more particularly, to an individualized electronic medical record system for providing a patient with a comprehensive collection of records, stored on CD rom or similar mobile storage device, that includes patient medical and family history, immunization records, information on any diagnosis and treatment from any physician, specialist, and hospital visits, test data in any media including video, surgeries, gene therapy, and other medical procedures, and medications (past and present), as well as adverse reactions or allergies to medications.

(2) Description of the Prior Art

In general, it is known in the art to use a medical records system that creates and maintains data electronically. Additionally, it is known in the art to include annotation in medical records and to incorporate paper files and mainframe data for a patient in electronic medical records. However, overall, these and related systems fail to provide any consideration for patient access to her/his personal information and records, which actually belong to the patient, in any media. Furthermore, generally, a given patient over her/his lifetime seeks medical care and treatment, for emergency medical care, for ongoing nonurgent conditions, and for maintenance of good health, from a broad range of medical care providers, diverse in specialty as well as geographic location. Due to the broad and disconnected geographic and temporal discontinuous medical care received by a patient, the patient's medical records are practically inaccessible and unmanageable by the patient and often the medical community at large. Even if access to the personal medical records by the patient were possible, the dissimilar forms and formats used by various medical care providers would make it unreasonable and nearly impossible to store the records in a single source, much less in an electronic format.

Typically, medical records systems for electronically storing data have been established and maintained on a mainframe computer, computer server or land area network within a medical provider's locality, e.g., hospital, doctor's office, laboratory, etc. Historically, individual patients have not had access to their own personal medical history and data, including diagnoses, treatments, medications, lab and other test results, like video imaging, X-rays, magnetic resonance imaging (MRI), CT scans, etc., prognoses, alternative treatments available, and the like. By way of example, it is known in the art to provide an electronic medical records system that creates and maintains all patient data electronically, including patient complaints, lab orders, medications, diagnoses, and procedures at its source at the time of entry using a graphical user interface having touch screens. Also, access to reference databases for consultation is included in the system. This and similar medical records systems is problematic because it does not provide the patient with unlimited access to her/his own medical records at any time. Furthermore, there exists a substantial risk of miscommunication, misunderstanding, lack of understanding or even lack of knowledge of past medical problems and procedures by the patient regarding her/his own medical background. Also, issues of patient privacy and concerns for privacy and data access arise, particularly in large systems.

Thus, existing electronic medical records systems inadequately addresses the problem and issue of providing unlimited, convenient and accurate access for the patient to her/his own medical records. Therefore, there remains a need for an individualized electronic medical record system for providing a patient with a comprehensive collection of her/his personal medical records and data, stored on CD rom or similar mobile storage device.

Additionally, other prior art medical records systems and/or methods for electronically storing patient medical records and data fail to provide means for the patient to have reasonably quick and easy access to the information and for patient-controlled maintenance and easy transport of comprehensive personal medical records, i.e. carrying medical records on the patient's person for travel and/or other medical visits to different physicians, specialists, and hospitals, and continuous transport of medical records available for access by emergency medical treatment service providers. For example, it is known in the art to provide a method for storing data to a central medical repository, the stored data being extracted from medical service record documents in any format from medical service providers. Alternatively, it is also known in the art to provide a method for automatic posting of medical insurance claims using a computerized data base system and data disposed in a known format. Also, it is known to provide an information exchange system for exchanging health care insurance information between an insurer and multiple health care providers. However, this type of system requires computer connection over a local area network and a proprietary database over the Internet for transfer of the information, and the patient does not have access to any of the information.

Finally, it is known in the art to provide a patient-based medical record system that electronically stores information on a portable storage device. However, such a system requires specialized reading devices and systems, without which the information is not accessible or readable. Furthermore, these systems do not provide means for converting text, image and other data formats to a format that is both storable and readable without requiring specialized reading apparatus. Conversion of a national or international health care system to use of electronic medical records stored on devices that require specialized reading devices is not economically feasible. Additionally, large institutions cannot and often will not agree upon a universal format; however, a patient-driven system can start immediately. Also, every patient would also be required to have such a reading device or have access to one in order to review her/his records. Thus, there remains a need for an individual patient-based and patient-controlled practical, effective and efficient electronic medical records system.

SUMMARY OF THE INVENTION

The present invention is directed to an individualized patient electronic medical records system that provides unlimited patient access to her/his medical records, including text and other data, including but not limited to lab results, EKGs, X-rays, video imaging, etc. Additionally, the invention may include a benchmark against which medical treatments can be evaluated for compliance with reasonable standard of care or a prompt to indicate appropriate testing, medications, etc., based upon the patient's age, sex, etc. Also, the invention is applicable to human patients and to animal patients. Advantages of the invention include patient ownership, control, and access to her/his individual records at any time. Also, the patient can review and enter comments or questions or self-reported data for assessment on her/his data record for review and consideration by a physician. Also, itemization of medical care providers comments, results, and data facilitate review by the patient as well as insurance providers, thereby preventing misunderstanding and fraud. Furthermore, the patient can carry the medical record on her/his person so that the information is readily accessible in the event of an emergency or if s/he were traveling. Finally, any entry to the medical records is coded or identified by the provider or patient her/himself, and a password or other write-protect means prevents tampering or altering information entered by someone else. However, access to the information by medical care providers and/or insurance providers and administrators, particularly emergency medical care providers, is not impeded by password or other protective means.

Thus, the present invention provides an individualized patient electronic medical records system for unlimited patient access to her/his personal and comprehensive medical records.

Accordingly, one aspect of the present invention is to provide an individualized patient electronic medical records system that provides unlimited patient access to her/his medical records, including text and other data. Still another aspect of the present invention is to provide an individualized patient electronic medical records system that provides unlimited patient access to her/his medical records, including text and other data stored on a portable electronic data and information storage device. Additionally, it is an aspect of the present invention to provide an individualized patient electronic medical records system that provides unlimited patient access to her/his medical records, including text and other data, which permits medical care providers and the patient to enter and record data in a readable format with encoding or other identification of date, time, and entity entering the data and/or information.

Also, it is an aspect of the present invention to provide a comprehensive electronic individual patient medical records system that identifies multiple users, particularly multiple medical care providers, and the treatments they perform or prescribe for the patient for review by insurance providers, including medicare, Medicaid, veterans administration, and other government-based providers, to prevent duplicate insurance filings and fraud.

Finally, it is an aspect of the present invention to provide the individual patient with full disclosure of and full access to individual patient medical records and history.

These and other aspects of the present invention will become apparent to those skilled in the art after a reading of the following description of the preferred embodiment when considered with the drawings.

DESCRIPTION OF THE PREFERRED EMBODIMENTS

Figure 1:
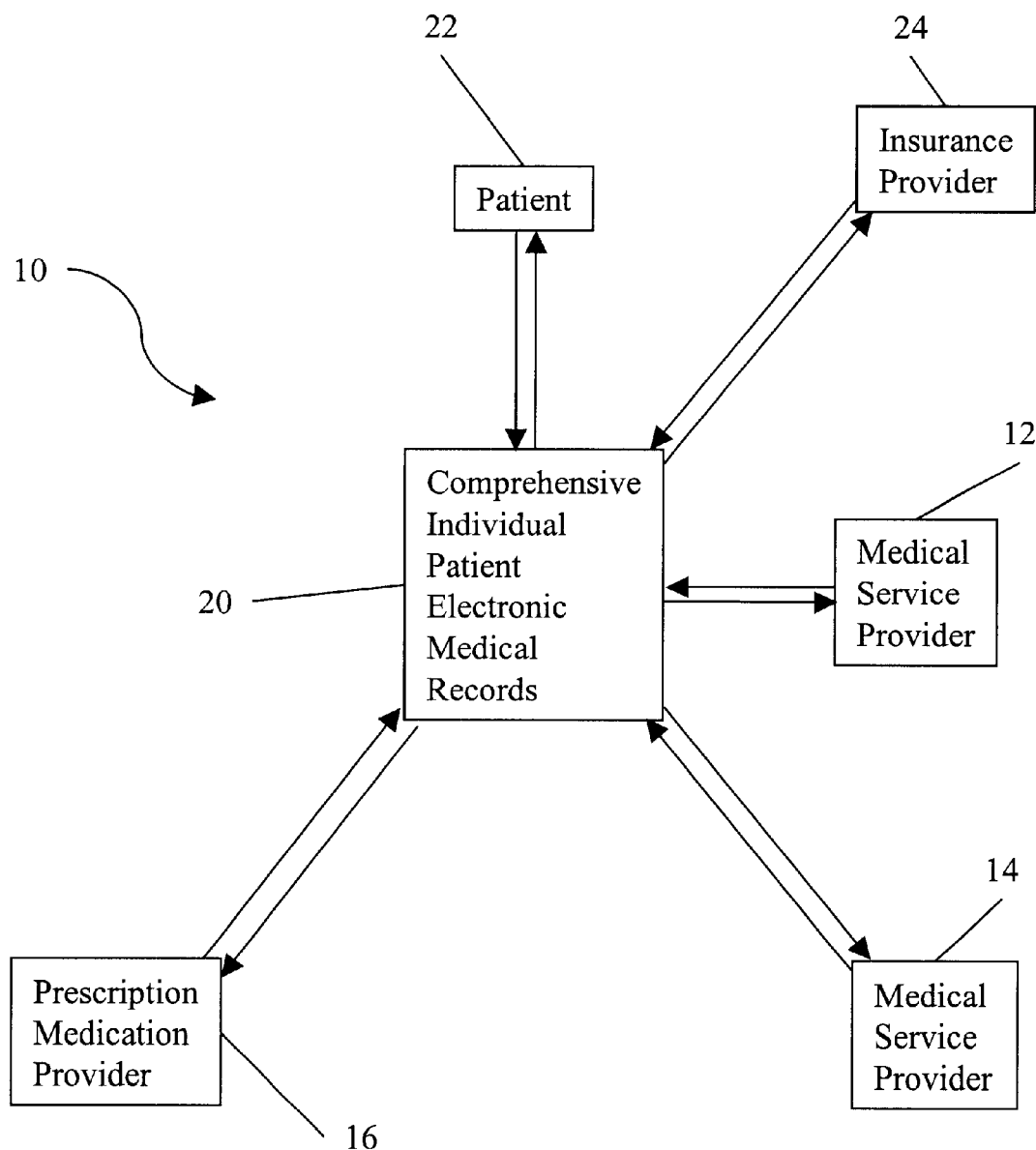
FIG. 1 is a block diagram illustrating the individualized patient medical records system architecture according to the present invention.

In the following description, like reference characters designate like or corresponding parts throughout the several views. Also in the following description, it is to be understood that such terms as "forward", "rearward", "left", "right", "upwardly", "downwardly", and the like are words of convenience and are not to be construed as limiting terms.

Referring now to the drawings in general and to FIG. 1 in particular, it will be understood that the illustrations are for the purpose of describing a preferred embodiment of the invention and are not intended to limit the invention thereto. For convenience, as best seen in FIG. 1, the individualized patient medical records system, generally referenced 10, the patient controls her/his comprehensive individual medical records recorded in an electronic mobile storage device 20, regardless of the point of care or identity of the medical care provider 12. Furthermore, multiple medical care providers 12, 14 can read the comprehensive individual patient medical records 20, which are capable of being stored electronically in text and non-text data format, or a combination thereof, via a computer and software. Preferably, the computer software is capable of universal application on computers used by multiple medical care providers and multiple users of the mobile electronic storage device for reviewing and recording information and data recorded thereon. This obviates repeating tests unnecessarily just to obtain patient data or information because previous test results are readily accessible by multiple users of the system, especially multiple medical care providers who are not located in the same facility. Also, the system according to the present invention prevents duplication of testing and prevents wasting time, resources, and money. The medical care providers 12, 14 can construct, write, and record information in the individualized patient medical records system 20. Preferably, the medical care providers will diagnose, identify and outline medical treatment and procedures, define prognosis, conduct necessary tests and procedures, review the results, and make notes or other comments on the patient and her/his condition and treatment, and then construct or write and then record electronically all of the information and data, both text and non-text format, on the mobile storage device for electronically recording and storing the comprehensive individualized patient medical records. The number, type, and location of medical care providers is not limited by the present invention; anyone having the standard computer and computer software program necessary for reading and writing records within the comprehensive individualized patient medical records system and having access to the electronic mobile storage device, which is preferably patient-owned and controlled, can utilize the system. According to the present invention, medical care providers and users of the electronic individualized patient medical records system are identified via identification means, more specifically by a passcode or bio-identification, including but not limited to fingerprint, DNA, retinal scan, etc. The user identification permits access to all or part of the patient records and permits or restricts access to read and write or to read-only.

In a preferred embodiment, the comprehensive individual patient medical records 20 are controlled by the patient 22, who has the capability of reading the medical records that are electronically stored on a mobile storage device 20 and who has the capability of writing comments or notes that are also recorded electronically with the comprehensive individualized patient medical records on the mobile storage device for the patient to review and comment on. In a preferred embodiment, the mobile storage device for electronically storing the patient medical records is portable. Also, in a preferred embodiment, the mobile storage device is a computer-based storage device, e.g., CD rom, diskette, tape, etc. Preferably, the mobile storage device is capable of storing both text and non-text data. Non-text data includes, but is not limited to, graphs, charts, X-rays, magnetic resonance imaging (MRI), CT scans, blood tests, video imaging, etc. In a preferred embodiment, the patient can record data and self-input data, including both text and non-text formats, including but not limited to weight, height, blood pressure, pacemaker data or signal, glucose levels, quality of life data, pain diary, etc. Peripheral devices may be required to input certain types of data, for example direct input of pacemaker signal data.

Additionally, a pharmacist or prescription medication dispensing agent 16 can also read the electronically recorded individualized patient medical records and write prescription-related information to be stored electronically in the records on the mobile storage device 20. In a preferred embodiment, the pharmacist or prescription medication dispensing agent would construct information on the patient relating to medications, i.e., type of medication, generic or brand-name medication, dosage amount, frequency and duration, allergic reactions, adverse reactions by the patient, potential side effects of the medication, potential reactions and/or interactions between different medications, etc.

Also in a preferred embodiment, as illustrated in FIG. 1, an insurance provider or administrator 24 can also read the electronically recorded individualized patient medical records and write insurance-related information to be stored electronically in the records on the mobile storage device 20. In a preferred embodiment, the insurance provider or insurance administrator would review information on the patient relating to insurance, i.e., treatment and procedure coverage under the insurance policy, insurance policy limitations and deductibles, etc. In a preferred embodiment, the medical care provider and treatment are identified by specific codes, e.g., ICD-9 codes, included in the electronic medical records system. Some codes, like ICD-9 codes may require regular updating to ensure the most current information. Preferably, these codes are encoded or encrypted so that they cannot be altered or eliminated by the medical care provider without consent or permission from the patient. These treatment and provider codes serve to prevent fraud in medical insurance filing, including government-based or—sponsored medical systems, e.g., Medicare and Medicaid. Preferably, electronic forwarding or transfer of the patient's electronic medical records from the system according to the present invention is possible; electronic transfer is particularly efficient for filing insurance and disability claims with respective providers after the patient has received treatment. Either the patient or the medical care provider may forward the required information, based upon the comprehensive individualized patient electronic medical records.

Also, in a preferred embodiment, the individualized patient medical records system includes a benchmark of medical guidelines or standards of care, such as those provided by the American Medical Association and the National Institutes of Health. More preferably, the medical guidelines include information specific to patient age, gender, race and other relevant information. Also, the medical guidelines include information to suggest or prompt the medical care provider to consider treatment options, necessary treatment or testing based upon the patient's medical condition, age, gender, and other predetermined information, e.g. travel requiring immunizations, etc., having an impact on the diagnoses and/or treatment decisions and alternatives for the patient, including alternative medical care providers. The medical guidelines or standards of care may be updated on a regular or non-regular basis, as necessary.

Figure 2:
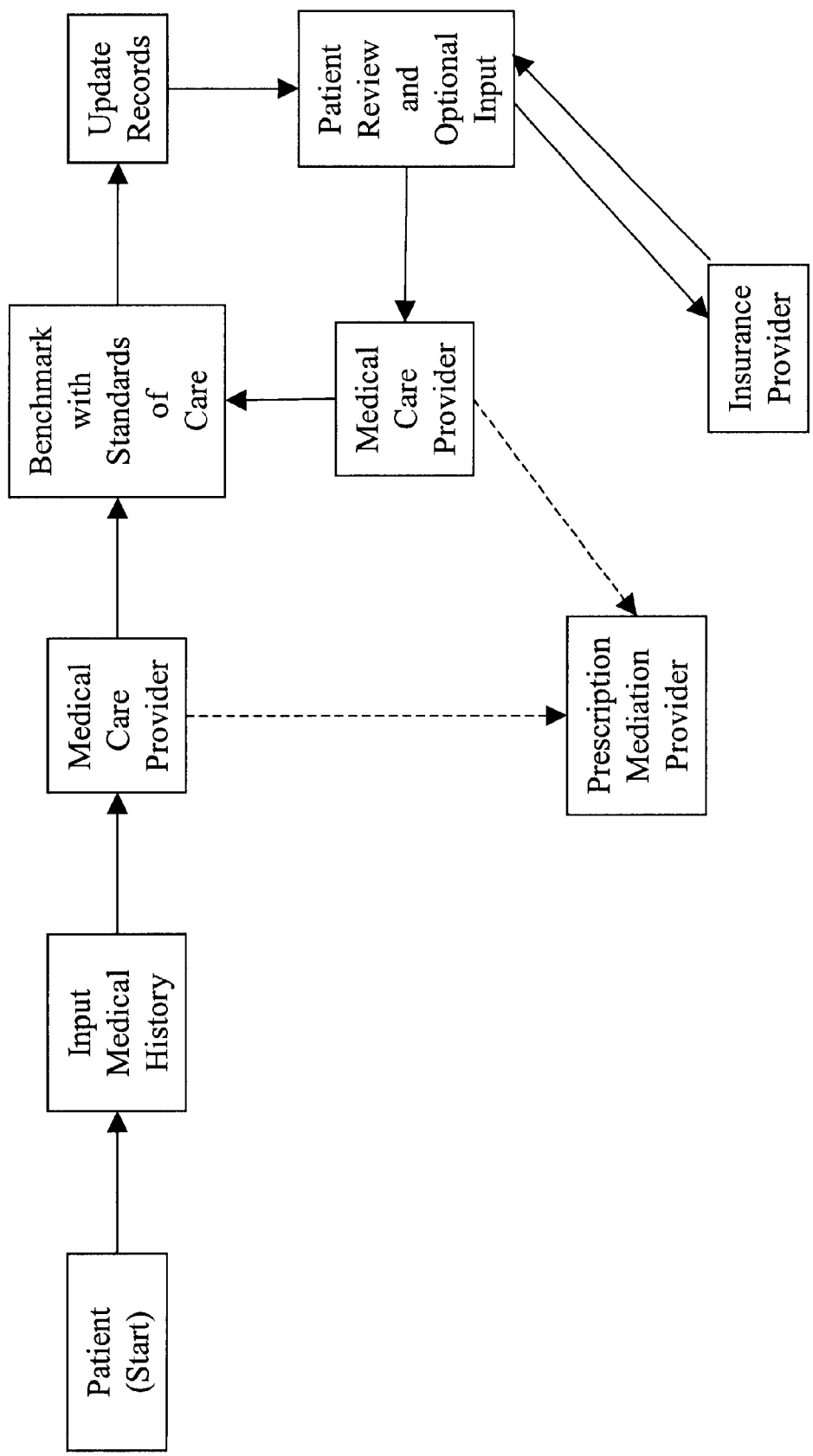
FIG. 2 is a flowchart illustrating the process flow of the individualized patient medical records system according to the present invention.

Referring now to FIG. 2, a preferred embodiment illustrated by a flowchart shows the method for recording information electronically on a mobile storage device for a comprehensive individual medical records system, generally referenced 30, according to the present invention. Preferably, the patient 32 owns and controls her/his individual comprehensive medical records stored electronically on a mobile storage device. Thus, the process starts with the patient having an electronic mobile storage device onto which the patient or her/his agent enters and records information on medical history, including genetic information and code, family history, known allergies (if any), current height, weight, age, donor status (including human leucocyte antigen (HLA) type, etc. Preferably, this information and data is recorded and encoded or otherwise identified, e.g., via passcode, fingerprint, voice recognition, retinal scan, or DNA, etc., as having been entered by the patient or patient's agent. Classification of the information and data entries and records, provider and/or user identification is preferably included in the medical records system according to the present invention. Based upon the classification within the records system, the information and data is indexed for easy access and reference. The indexing system may include categorization of text and non-text data, graph and other formats for convenient and efficient review of the information and data.

Next, when the patient needs medical care or treatment, s/he contacts a first medical care provider 36 for examination, observation, care or treatment. The patient brings the comprehensive individualized patient medical records electronically stored on a mobile storage device with her/him to the medical care provider 36. After visiting the first medical care provider, the medical care provider diagnoses, identifies and outlines medical treatment and procedures, defines prognosis, conducts necessary tests and procedures, reviews the results, and makes notes or other comments on the patient and her/his condition and treatment and then records the information on the mobile storage device. Next, a benchmark comparison step 40 permits the medical care provider to compare the proposed diagnosis and treatment to guidelines or standards of care that consider the patient's age, gender, medical history, etc. Next, the individualized patient medical records are updated in an updating step 42 to document the comparison with guidelines, thereby indicating if a deviation from the recognized standard of care exists. Thus, the system can effective guard against medical malpractice or substantial deviations from guidelines or recognized standards of care for any medical condition. Next in a reviewing step 44, the patient reviews and can write comments or notes to be included in the comprehensive medical record. If necessary, then the patient can forward the records or a part thereof, encrypted or otherwise coded, electronically to an insurance provider in an insurance step 46. Also, if necessary, the patient can forward the records or a part thereof electronically to a pharmacist or prescription medication provider in a prescription medication step 48. Finally, the process can be repeated with the same or different medical care provider, beginning with step 38 or 50, respectively, depending upon the medical care needed or sought by the patient.

The present invention described in the foregoing is preferably applicable to human patients. Alternatively, and also preferably, the electronic comprehensive individualized patient medical records system may be used for animals as well. In the event that the system is used for animals instead of human patients, the medical care providers are veterinarians and the animal's owner instead of the animal owns, controls, reads, reviews, writes and records information and data in the electronic records. Furthermore, the insurance step and prescription medication step of FIG. 2 are unnecessary for, and are preferably not included in, the electronic individualized medical records system for animal patients, except where insurance is available.

The foregoing preferred embodiments describe and illustrate the comprehensive individualized patient medical records system according to the present invention.

Certain modifications and improvements will occur to those skilled in the art upon a reading of the foregoing description but are not included for the sake of conciseness. By way of example, changes in technology may provide portable storage device options not specifically mentioned in the foregoing description, but which provide equivalent functions. Also, various software and hardware configurations and arrangements may also change rapidly as developments in the industry so necessitate. It should be understood that all such modifications and improvements have been deleted herein for the sake of conciseness and readability but are properly within the scope of the following claims.

I claim:

1. An electronic medical records system comprising:

medical information and data specific to a patient, including a medical professional-based input having information entered by at least one medical professional and a patient-based input having patient comments and information provided by the patient, wherein the medical professional-based input is not entered by the patient and wherein the patient comments and information provided by the patient are not entered by a medical professional;

a computer and connected peripheral devices for entering the medical information and data into electronic format; and an electronic data storage device onto which the medical information and data are recorded via computer software, wherein the computer software includes identification means for identifying users and for permitting access and input based upon the identification of the user, particularly distinguishing medical professionals from the patient and permitting only patient-based input to be entered by the patient and permitting only medical professional-based input to be entered by medical professionals, thereby providing an individual patient with unlimited read access and limited input of patient-based information directly to her/his personal medical records.

2. The electronic medical records system according to claim 1, wherein the electronic data storage device permits the medical information and data to be reviewed and to be modified.

3. The electronic medical records system according to claim 1, wherein the medical information and data forms a comprehensive medical record for an individual patient.

4. The electronic medical records system according to claim 1, wherein the electronic data storage device is mobile.

5. The electronic medical records system according to claim 1, wherein the electronic data storage device is portable.

6. The electronic medical records system according to claim 5, wherein the electronic data storage device is a CD rom.

7. The electronic medical records system according to claim 5, wherein the electronic data storage device is a series of CD roms.

8. The electronic medical records system according to claim 5, wherein the electronic data storage device is a diskette.

9. The electronic medical records system according to claim 5, wherein the electronic data storage device is a series of diskettes.

10. The electronic medical records system according to claim 5, wherein the electronic data storage device is a computer chip.

11. The electronic medical records system according to claim 5, wherein the electronic data storage device is a palm-sized computer.

12. The electronic medical records system according to claim 5, wherein the electronic data storage device is a tape.

13. The electronic medical records system according to claim 1, wherein the medical records are text.

14. The electronic medical records system according to claim 1, wherein the medical records are text and non-text data.

15. The electronic medical records system according to claim 1, wherein the patient is a human being.

16. The electronic medical records system according to claim 1, wherein the patient is an animal.

17. The electronic medical records system according to claim 1, further including a medical history for the individual patient.

18. The electronic medical records system according to claim 17, wherein the medical history further includes family medical history.

19. The electronic medical records system according to claim 17, wherein the medical history further includes genetic information for the individual patient.

20. The electronic medical records system according to claim 18, wherein the genetic information includes a DNA code for the patient.

21. The electronic medical records system according to claim 17, further including immunization records for the patient.

22. The electronic medical records system according to claim 1, further including a listing of required future immunizations for the patient.

23. The electronic medical records system according to claim 1, further including a schedule for future immunizations.

24. The electronic medical records system according to claim 17, further including suggested diagnosis and recommended treatment and testing for hereditary diseases.

25. The electronic medical records system according to claim 1, further including benchmark information for making a comparison of the medical information and data with recognized standards of medical care.

26. The electronic medical records system according to claim 25, wherein the benchmark information is automatically checked against the medical information and data.

27. The electronic medical records system according to claim 17, wherein the medical history further includes medications taken by the patient.

28. The electronic medical records system according to claim 27, further including adverse reactions known for the individual patient.

29. The electronic medical records system according to claim 27, further including known allergies of the patient.

30. The electronic medical records system according to claim 1, wherein the computer software enables multiple users to enter and record the medical information and data onto the storage device and to review the recorded information and data.

31. The electronic medical records system according to claim 1, wherein the the multiple users comprise at least one medical care provider, a prescription medication provider, an insurance provider, and the individual patient.

32. The electronic medical records system according to claim 1, further including emergency access for emergency medical care providers.

33. The electronic medical records system according to claim 1, wherein the identification means comprises a passcode.

34. The electronic medical records system according to claim 1, wherein the identification means comprises bio-identification.

35. The electronic medical records system according to claim 1, wherein the identification means is a fingerprint.

36. The electronic medical records system according to claim 1, wherein select users have read-only access to the medical records.

37. The electronic medical records system according to claim 1, wherein the information and data recorded is encoded upon entry and recordation, thereby providing classification means for the information and data.

38. The electronic medical records system according to claim 37, further including an index of information and data recorded on the storage device.

39. The electronic medical records system according to claim 37, further including a date and a time for the information and data.

40. The electronic medical records system according to claim 1, wherein the information and data is encrypted for protection from unauthorized users.

41. The electronic medical records system according to claim 1, wherein the software has a universal format thereby permitting many different types of computer systems to read and write information and data for recordation on the electronic data storage device.

42. A method for creating an electronic comprehensive patient medical records system comprising the steps of:

a patient acquiring a mobile electronic data storage device;

the patient entering and recording only patient-based information, including the patient's information relevant to the patient's medical history and patient comments using a computer and software onto the mobile electronic data storage device;

the patient receiving medical care from at least one medical care provider;

the at least one medical care provider reviewing the patient medical history and diagnosing and treating the patient;

the at least one medical care provider comparing the diagnosis and treatment with a benchmark having a recognized standard of care;

the at least one medical care provider updating the records by inputting medical professional-based information;

the patient reviewing the medical care provider's data in a read only format;

the patient writing patient-based input comments and recording the comments on the storage device;

the patient forwarding the records to an insurance provider for review and for providing insurance coverage; and the patient forwarding the records to a prescription medication provider for review and for filling prescriptions for medications.

43. The method according to claim 42, further including the step of updating the records based on the patient's medical history and genetic code to suggest diagnosis and recommended treatment and testing for diseases to which the patient may have a propensity.

44. The method according to claim 42, further including a step of updating the records with benchmark information for making a comparison of the medical information and data with recognized standards of medical care.

45. The method according to claim 44, further including a step of automatically checking the benchmark information against the medical information and data.

46. The method according to claim 42, further including a step of identifying the users for permitting access to records based upon the identification.

47. The method according to claim 46, further including a step of allowing emergency access for emergency medical care providers.

48. The method according to claim 46, wherein the users are identified by a passcode.

49. The method according to claim 46, wherein the users are identified by bio-identification.

50. The method according to claim 46, wherein the users are identified by fingerprint.

51. The method according to claim 46, wherein select users have read-only access to the medical records, including the patient having read-only access to medical professional based input.

52. The method according to claim 42, further including a step of encoding the information and data upon entry and recordation, thereby providing classification means for the information and data.

53. The method according to claim 52, further including a step of providing an index of information and data recorded on the storage device.

54. The method according to claim 52, further including a step of providing a date and a time for the information and data.

55. The method according to claim 42, further including a step of encrypting the information and data for protection from unauthorized users.

56. The method according to claim 42, further including a step of formatting the information and data in a universal format thereby permitting many different types of computer systems to read and write information and data for recordation on the electronic data storage device.

* * * * *